US011064872B2

United States Patent
Hatano et al.

(10) Patent No.: US 11,064,872 B2
(45) Date of Patent: Jul. 20, 2021

(54) BENDING OPERATION DEVICE AND ENDOSCOPE WITH THE SAME APPLIED THERETO

(71) Applicant: Olympus Corporation, Hachioji (JP)

(72) Inventors: Keisuke Hatano, Koganei (JP); Kiwamu Fujitani, Orefield, PA (US)

(73) Assignee: OLYMPUS CORPORATION, Tokyo (JP)

( * ) Notice: Subject to any disclaimer, the term of this patent is extended or adjusted under 35 U.S.C. 154(b) by 331 days.

(21) Appl. No.: 16/131,654

(22) Filed: Sep. 14, 2018

(65) Prior Publication Data

US 2019/0014973 A1    Jan. 17, 2019

Related U.S. Application Data

(63) Continuation of application No. PCT/JP2016/078616, filed on Sep. 28, 2016.

(30) Foreign Application Priority Data

Mar. 17, 2016   (JP) .............................. JP2016-053502

(51) Int. Cl.
  *A61B 1/00*    (2006.01)
  *A61B 1/005*   (2006.01)
  *G02B 23/24*   (2006.01)

(52) U.S. Cl.
  CPC .......... *A61B 1/0057* (2013.01); *A61B 1/0052* (2013.01); *G02B 23/2476* (2013.01)

(58) Field of Classification Search
  CPC .......... A61B 1/00066; A61B 2017/003; A61B 2017/00318; A61B 2017/00323;
  (Continued)

(56) References Cited

U.S. PATENT DOCUMENTS

2003/0092965 A1    5/2003    Konomura et al.
2008/0275302 A1    11/2008    Hosaka
(Continued)

FOREIGN PATENT DOCUMENTS

CN    102188220 A    9/2011
JP    58-064301    4/1983
(Continued)

OTHER PUBLICATIONS

International Search Report and Written Opinion from corresponding International Application No. PCT/JP2016/078616, dated Nov. 29, 2016.
(Continued)

*Primary Examiner* — Michael J Carey
*Assistant Examiner* — Christen Hicks
(74) *Attorney, Agent, or Firm* — Oliff PLC

(57) ABSTRACT

A bending operation device includes a bending operation member, a bendable part, an operation wire, a pulling wire, and a connection member. The bending operation member is disposed in an operation unit and is supported tiltably in a preset direction. The bendable part is disposed on a side of a distal end of the operation unit. The operation wire is connected at an end thereof to the bending operation member and is pulled or relaxed according to displacement of the bending operation member. The pulling wire is connected to the bendable part and bends the bendable part. The connection member is connected to the operation wire at a first position and is connected to the pulling wire at a second position. The second position is shifted from the first position by a preset angle in a turning direction about a longitudinal axis of the operation unit.

14 Claims, 12 Drawing Sheets

(58) Field of Classification Search
CPC .......... A61B 2017/00327; A61B 1/005; A61B 1/0051; A61B 1/0052; A61B 1/0553; A61B 1/0056; A61B 1/0057; A61M 25/0133; A61M 25/0136; A61M 25/0147; F16H 21/52; G02B 23/2476
USPC ................................................ 600/149, 150
See application file for complete search history.

(56) References Cited

U.S. PATENT DOCUMENTS

| | | | |
|---|---|---|---|
| 2013/0047755 | A1 | 2/2013 | Okamoto |
| 2013/0338441 | A1* | 12/2013 | Okamoto ............. A61B 1/0057 600/146 |
| 2016/0309985 | A1 | 10/2016 | Akui |

FOREIGN PATENT DOCUMENTS

| | | |
|---|---|---|
| JP | 04-367643 | 12/1992 |
| JP | 04367643 A * | 12/1992 |
| JP | 2002-264048 | 9/2002 |
| JP | 2003-325437 | 11/2003 |
| JP | 2007-325958 | 12/2007 |
| JP | 2009-005836 | 1/2009 |
| JP | 2009-160204 | 7/2009 |
| WO | 2012117836 | 9/2012 |
| WO | 2015174139 | 11/2015 |

OTHER PUBLICATIONS

Japanese Office Action JP 2017-521014, dated Jul. 14, 2017.

\* cited by examiner

BENDING OPERATION DEVICE AND ENDOSCOPE WITH THE SAME APPLIED THERETO

CROSS-REFERENCE TO RELATED APPLICATIONS

This application is a continuation application of PCT Application No. PCT/JP2016/078616 filed on Sep. 28, 2016, which in turn claim priority to the Japanese Patent Application No. 2016-053502 filed on Mar. 17, 2016 in Japan which is hereby incorporated by reference in its entirety.

TECHNICAL FIELD

The technology disclosed herein generally relates to operation of an endoscope and more particularly, a bending operation device which allows a bendable part to undergo bending motion in response to tilting operation of a bending operation member, and an endoscope.

DESCRIPTION OF THE RELATED ART

To observe subjects or objects that are difficult to be observed from the outside, such as the insides of living bodies or the insides of structures, endoscopes have conventionally found wide-spread utility, for example, in the medical field or industrial field. The endoscopes enable internal observations by inserting of insertion sections having observation means accommodated therein into the subjects or objects. The insertion section of an endoscope of the above-mentioned type includes a bendable part so as to provide the endoscope (i) with improved insertion maneuverability into a subject or an object under examination or treatment and also (ii) with improved observation convenience. The bendable part is configured to be bendable in the vicinity of a tip portion of the endoscope. This bendable part is bent by a bending operation device disposed in an operation unit.

As bending operation devices for operating, specifically bending the bendable parts of the insertion sections in conventional endoscopes, there are bending operation devices of various shapes such as, for example, (i) those of the type that a rod-shaped, bending operation member such as joystick is tiltable and (ii) those of the type that a bending operation member in the form of a rotary dial (operation knob) is rotatable. For example, the bending operation device disclosed in Japanese Patent Laid-Open No. 2007-325958 or the like has a joystick-type bending operation member. A bending operation device of such a type is configured of various component members including a bending operation member. Among these component members, the most parts of the component members other than the bending operation member are within an operation unit. Further, wire members are inserted and disposed in the operation unit and an insertion section. The wire members connect the bending operation member and a bendable part to one another.

Within the operation unit of the conventional endoscope, various other components are also accommodated and disposed. Other components include, for example, (i) component members of a suction mechanism that operates in response to suction operation, (ii) component members of an air-feed/water-feed mechanism that operates in response to air feed operation or water feed operation, and the like. Similar to the wire members described hereinbefore, a suction tube, an air feed tube, water feed tube and the like as well as a light guide from a light source device are also inserted and disposed in the operation unit and insertion section. In the conventional endoscope, the various component members are attachably disposed within the operation unit as described hereinbefore. When downsizing the operation unit, some contrivance is needed to efficiently arrange the various component members inside the operation unit. However, the wire members of the bending operation device in the conventional endoscope are configured to be movable in the direction of an axis of insertion. Therefore, it is necessary to arrange the wire members while avoiding interference with other attached component members, for example, the suction tube and the like.

In a conventional bending operation device, when wire members connect a bending operation member and a bendable part, for example, a configuration is adopted so as to avoid interference of the wire members with other component members in an operation unit by contriving the arrangement of the wire members inside the operation unit. First example of the configuration is adopted by disposing a "pull direction changing member" that changes the pulling direction of the wire members. Second example of the configuration is adopted by arranging the wire members in an oblique direction relative to the direction of tilting (the positive, upward, downward, leftward or rightward direction) of the bending operation member. However, with the configuration of the second example, it is also necessary to similarly arrange wire members that extend through an insertion section. This configuration, therefore, imposes a restriction to the layout of various components inside the insertion section. Also, this configuration leads to possibility of causing an impediment to a reduction in the diameter of the insertion section.

BRIEF SUMMARY OF EMBODIMENTS

A bending operation device according to one aspect of the present disclosure includes a bending operation member, a bendable part, an operation wire, a pulling wire, and a connection member. The bending operation member is disposed in an operation unit and is supported tiltably in a preset direction. The bendable part is disposed on a side of a distal end of the operation unit. The operation wire is connected at an end thereof to the bending operation member and is configured to be pulled or relaxed according to displacement of the bending operation member. The pulling wire is connected at a distal end thereof to the bendable part and is configured to bend the bendable part when pulled or relaxed. The connection member is connected to an opposite end of the operation wire at a first position and is connected to a proximal end of the pulling wire at a second position. The second position is shifted from the first position by a preset angle in a turning direction about a longitudinal axis of the operation unit. The connection member is held displaceable according to pulling or relaxing of the operation wire.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

DETAILED DESCRIPTION OF THE EMBODIMENTS

Figure 1:
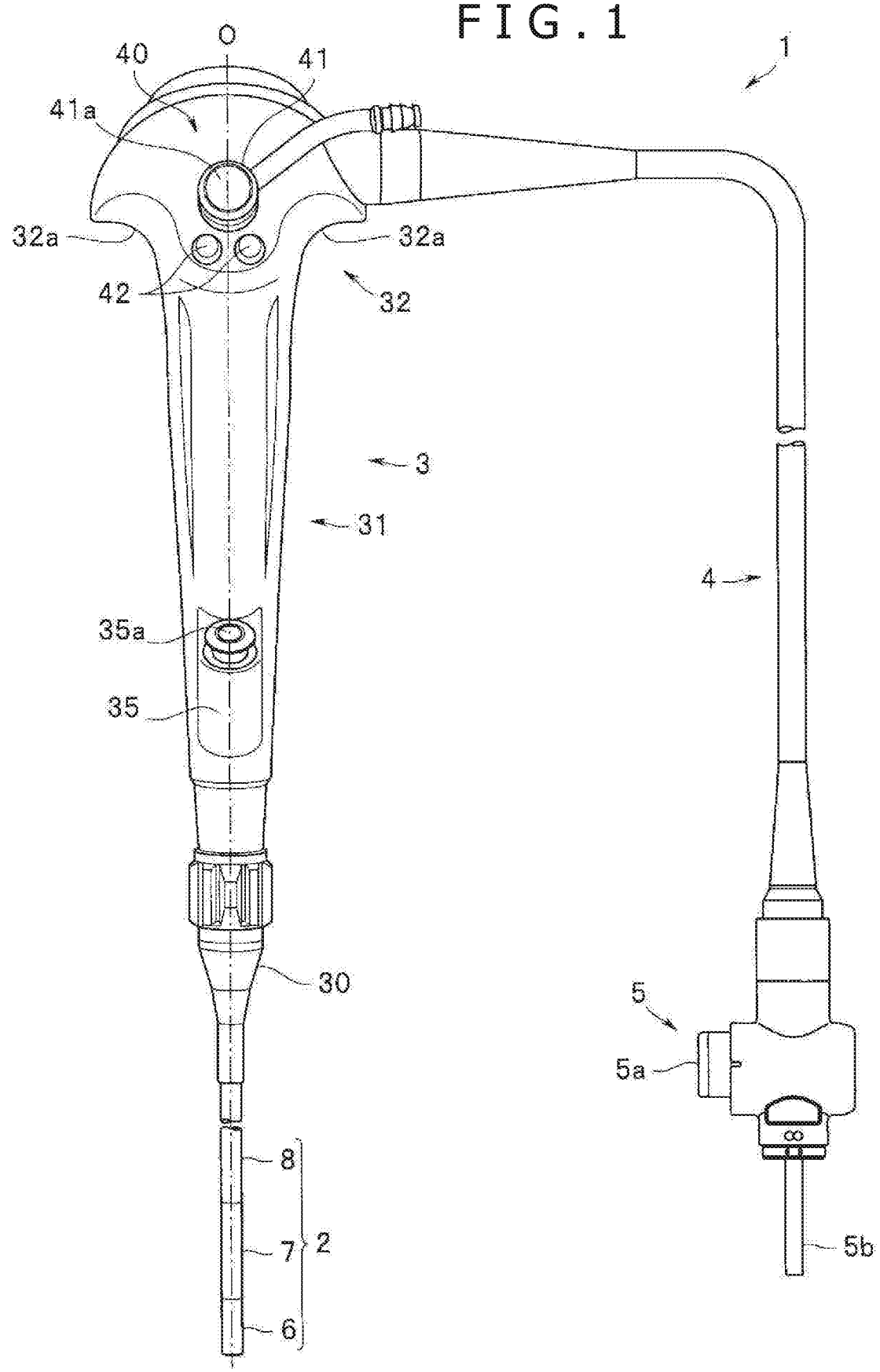
FIG. 1 is a front view illustrating an appearance of an endoscope including a bending operation device according to an embodiment of the present disclosure.

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

With the foregoing in view, the present disclosure has as aspects thereof the provision of a bending operation device of an endoscope. The bending operation device allows a bendable part to undergo bending motion in response to tilting operation of a bending operation member. The endoscope includes the bending operation device within an operation unit. Both the bending operation device and the endoscope have a configuration capable of widening the freedom of arrangement of wire members in the operation unit and an insertion section by realizing, with a simple configuration, a mechanism that helps to change the pulling direction of the wire members by the bending operation device while suppressing an increase in the size of the operation unit.

To achieve the above-described aspects, a bending operation device according to one aspect of the present disclosure includes a bending operation member, a bendable part, an operation wire, a pulling wire, and a connection member. The bending operation member is disposed in an operation unit and supported tiltably in a preset direction. The bendable part is disposed on a distal end of the operation unit. The operation wire is connected at an end thereof to the bending operation member and is configured to be pulled or relaxed according to displacement of the bending operation member. The pulling wire is connected at a distal end thereof to the bendable part and is configured to bend the bendable part when pulled or relaxed. The connection member has a first position and a second position. The second position is shifted from the first position by a preset angle in a turning direction about a longitudinal axis of the operation unit. The operation wire is connected to an opposite end thereof to the first position. The pulling wire is connected at a proximal end thereof to the second position. The connection member is held displaceable according to pulling or relaxing of the operation wire.

An endoscope according to another aspect of the present disclosure includes an operation unit, an insertion section, and the bending operation device inside the operation unit. The insertion section is disposed consecutively on a distal end of the operation unit and is formed in a shape of a slender tube. According to the present disclosure, it is possible to provide a bending operation device and an endoscope. The bending operation device allows a bendable part to undergo bending motion in response to tilting operation of a bending operation member. The endoscope includes the bending operation device within the operation unit. Both of the bending operation device and the endoscope have a configuration capable of widening the freedom of arrangement of wire members in the operation unit and an insertion section by realizing, with a simple configuration, a mechanism that helps to change the pulling direction of the wire members by the bending operation device while suppressing an increase in the size of the operation unit.

The present disclosure will hereinafter be described based on an embodiment and alternatives modifications thereof illustrated in the drawings. It is, however, to be noted that the individual drawings to be used in the following description are schematic illustrations. The dimensional relations, reduction scales and the like of individual members may be illustrated differently depending on the respective elements of configuration to depict each element of configuration in a size of such a degree as to be recognizable. Concerning (i) the numbers and shapes of the elements of configuration, (ii) the ratio in size of the elements of configuration, (iii) the relative positional relationship of the elements of configuration, and the like illustrated in these individual drawings, the present disclosure, therefore, should not be limited only to the illustrated embodiment and modifications.

Figure 2:
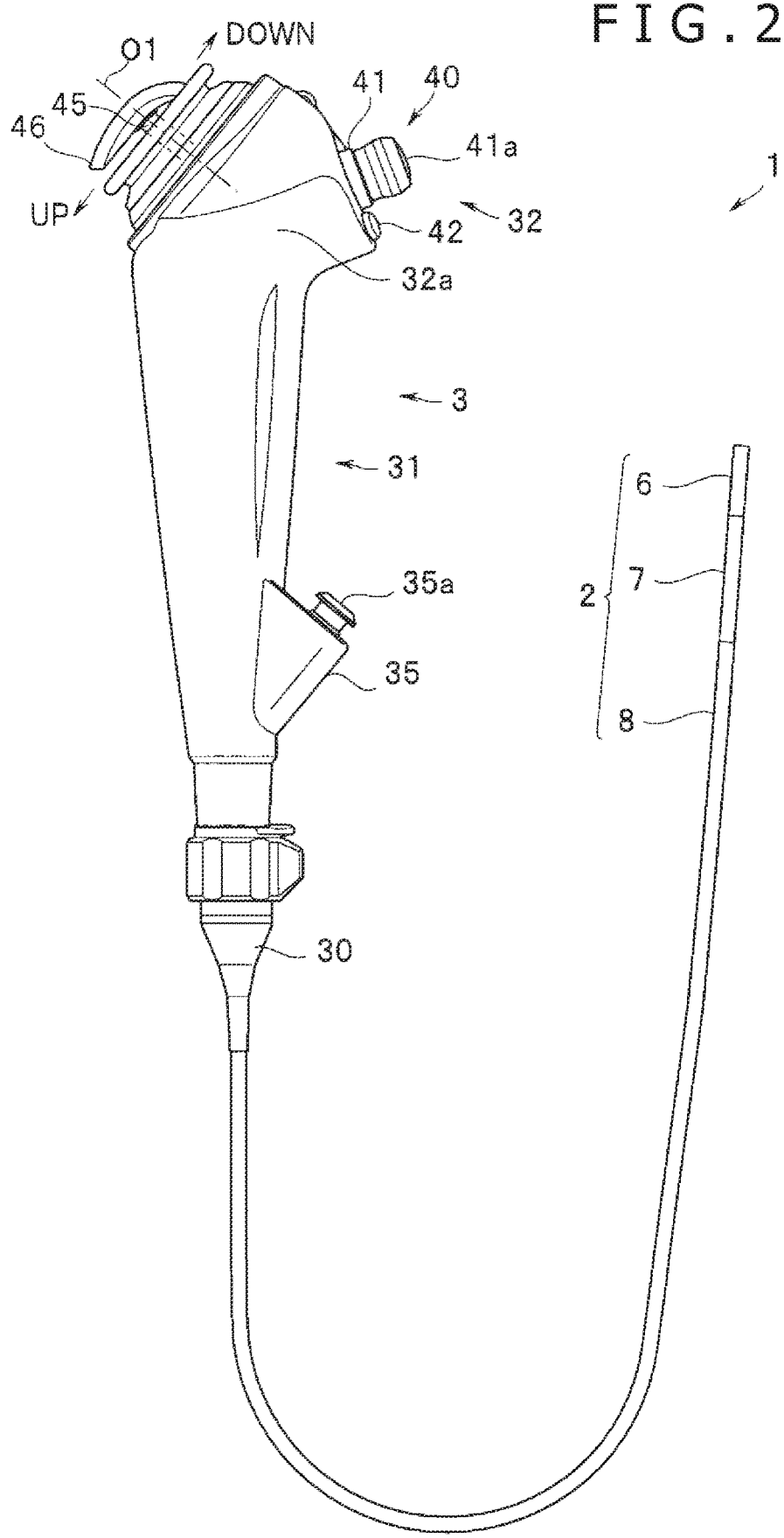
FIG. 2 is a right side view illustrating the appearance of the endoscope of FIG. 1.

The endoscope of this embodiment is a bronchial endoscope 1. As illustrated in FIGS. 1 and 2, this endoscope 1 includes an insertion section 2, an operation unit 3, a universal cord 4, and an endoscope connector 5. The insertion section 2 is formed in the shape of a slender tube. The operation unit 3 is disposed consecutively on a proximal end of the insertion section 2. The universal cord 4 is not illustrated in FIG. 2. The universal cord 4 is used as an endoscope cable disposed extending from the operation unit 3. The endoscope connector 5 is not illustrated in FIG. 2. The endoscope connector 5 is disposed on a distal end of the universal cord 4. The insertion section 2 includes a tip portion 6, a bendable part 7 and a flexible tube part 8, all of which are disposed consecutively in this order from the proximal end of the insertion section 2. The insertion section 2 is configured by a tubular member having flexibility as a whole. In other words, the bendable part 7 may be considered to be a configuration member disposed on the side of a distal end of the operation unit 3 and disposed on the side of the distal end of the insertion section 2. The operation unit 3 includes a bend preventing portion 30, a grip handle 31 and an operation unit main body 32. The bend preventing portion 30 is connected to the flexible tube part 8 in a state that the flexible tube part 8 is covered at a proximal end thereof with the bend preventing portion 30. The grip handle 31 is disposed consecutively with the bend preventing portion 30 and can be held by the user. The operation unit main body 32 is disposed consecutively on the side of a proximal end of the grip handle 31. It is to be noted that in this embodiment, directions about an insertion axis "O" (see FIG. 1) in the operation unit 3 are defined based on a state that the user holds the grip handle 31. Specifically, with respect to the operation unit 3, front, rear, left and right directions ("front" wall, "rear" wall and "left" and "right" walls, and so on) are defined as viewed from the user who holds the grip handle 31.

As illustrated in FIG. 1, the grip handle 31 of the operation unit 3 is formed in a horizontally-symmetrical shape with respect to the insertion axis "O" or central axis. Therefore, the user can similarly hold the grip handle 31 with either of left or right hand. On a front wall on the side of a distal end of the grip handle 31, a surgical instrument insertion part 35 is disposed. This surgical instrument insertion part 35 includes a surgical instrument insertion port 35*a*. A surgical instrument (not shown) for a desired treatment site can be inserted through the surgical instrument insertion port 35*a*. The operation unit main body 32 of the operation unit 3 has a shape that bulges to the left and right sides symmetrically with respect to the insertion axis "O". On left and right side walls on the side of a distal end of the operation unit main body 32, guide recesses 32*a* are formed to guide the index finger or the like of the user, who holds the grip handle 31, to operation buttons 40. The surgical instrument insertion port 35*a* is in communication with a surgical instrument insertion channel 13 via an unillustrated branch member inside the operation unit 3. The surgical instrument insertion channel 13 is described hereinafter in FIG. 4. Further, at the surgical instrument insertion part 35, an unillustrated forceps plug is detachably disposed. The forceps plug is a lid member for closing up the surgical instrument insertion port 35*a*.

On the side of the proximal end of the grip handle 31, the operation unit main body 32 is configured of a hollow member of a substantially partial-spherical shape that bulges primarily to the left and right sides and also frontward. On the side of a front wall of the operation unit main body 32, the operation buttons 40 are formed to perform various functions of the endoscope 1. These buttons 40 include, for non-limiting example, a suction button 41*a* and two button switches 42. The suction button 41*a* projects from a suction valve 41 detachably attached to the operation unit main body 32. Desired ones of the various functions of the endoscope 1 can be allocated to the two button switches 42. These suction button 41*a* and button switches 42 are arranged so that they become horizontally symmetrical on the side of the front wall of the operation unit main body 32. Described specifically, the suction button 41*a* in this embodiment is arranged centrally in the horizontal width direction of the operation unit main body 32 so that the suction button 41*a* lies on the insertion axis "O". On the other hand, the two button switches 42 are arranged at horizontally symmetrical positions, with the insertion axis "O" being flanked therebetween, on a side more distal than the suction button 41*a*.

Figure 3:
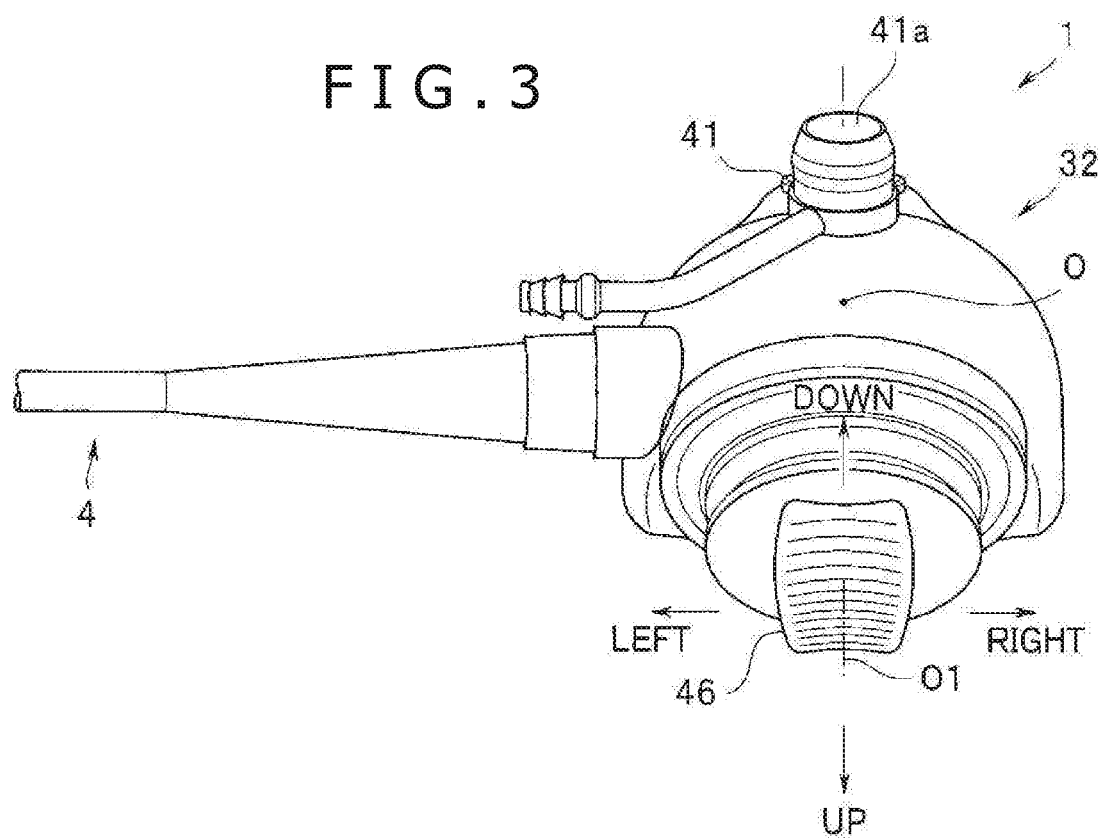
FIG. 3 is a top view illustrating the operation unit main body portion of the endoscope depicted in FIG. 1.

As illustrated in FIG. 2, on the side of the rear wall of the operation unit main body 32, a bending lever 45 is disposed (not illustrated in FIGS. 1 and 3) as an operation lever for use in performing bending operation on the bendable part 7. This bending lever 45 is configured to be tiltable about a sign O1 depicted in FIGS. 2 and 3, specifically a lever axis O1 of the bending lever 45. In other words, the bending lever 45 is used as a bending operation member, which is disposed on the operation unit 3 and is supported tiltably in a preset direction. As the direction of tilting of the bending lever 45, as illustrated in FIG. 3, for example, the left-right direction of tilting operation is defined in the horizontal width direction of the operation unit 3. The horizontal width direction is a direction orthogonal to the insertion axis "O". The up-down direction is defined in a direction orthogonal to the horizontal width direction. More specifically, leftward tilting direction, rightward tilting direction, upward tilting direction, and downward tilting direction are depicted as examples of the direction of tilting of the bending lever 45 in this embodiment. Direction to the left side of the sheet of FIG. 3 is defined to be the direction of tilting as the leftward tilting direction for bending the bendable part 7 leftward. Direction to the right side of the sheet of FIG. 3 is defined to be the direction of tilting as the rightward tilting direction for bending the bendable part 7 rightward. Direction to the lower side of the sheet of FIG. 3 is defined to be the direction of tilting as the upward tilting direction for bending the bendable part 7 upward. Direction to the upper side of the sheet of FIG. 3 is defined to be the direction of tilting as the downward tilting direction for bending the bendable part 7 downward.

On a pointed end portion of the bending lever 45, a finger rest 46 is arranged in FIGS. 2 and 3. The user's thumb or the like can be kept in contact with the finger rest 46. From a side part (for example, the left side part) of this operation unit main body 32, the universal cord 4 extends. This universal cord 4 is a composite cable. Various signal lines and the like are (i) internally inserted through the universal cord 4, (ii) extending through the insertion section 2 from the side of the tip portion 6 to the operation unit 3 and (iii) further extending from the operation unit 3. A light guide (not illustrated) from a light source device (not illustrated) is inserted through the universal cord 4. An air-feed/water-feed tube is also inserted through the universal cord 4 and extending from an air-feed/water-feed device (not illustrated). The endoscope connector 5 is disposed on a distal end of the universal cord 4 in FIG. 1. The endoscope connector 5 has an electric connector adapter 5*a* on a side wall part thereof. The endoscope connector 5 also has a light source connector adapter 5*b*. A signal cable is to be connected to the electric connector adapter 5*a*. The signal cable serves to connect between a video processor (not illustrated) as an external device and the electric connector adapter 5*a*. On the other hand, the light guide and electric cables are connected to the light source connector adapter 5*b*. The light guide helps to connect between the light source device as an external device and the light source connector adapter 5*b*.

Figure 4:
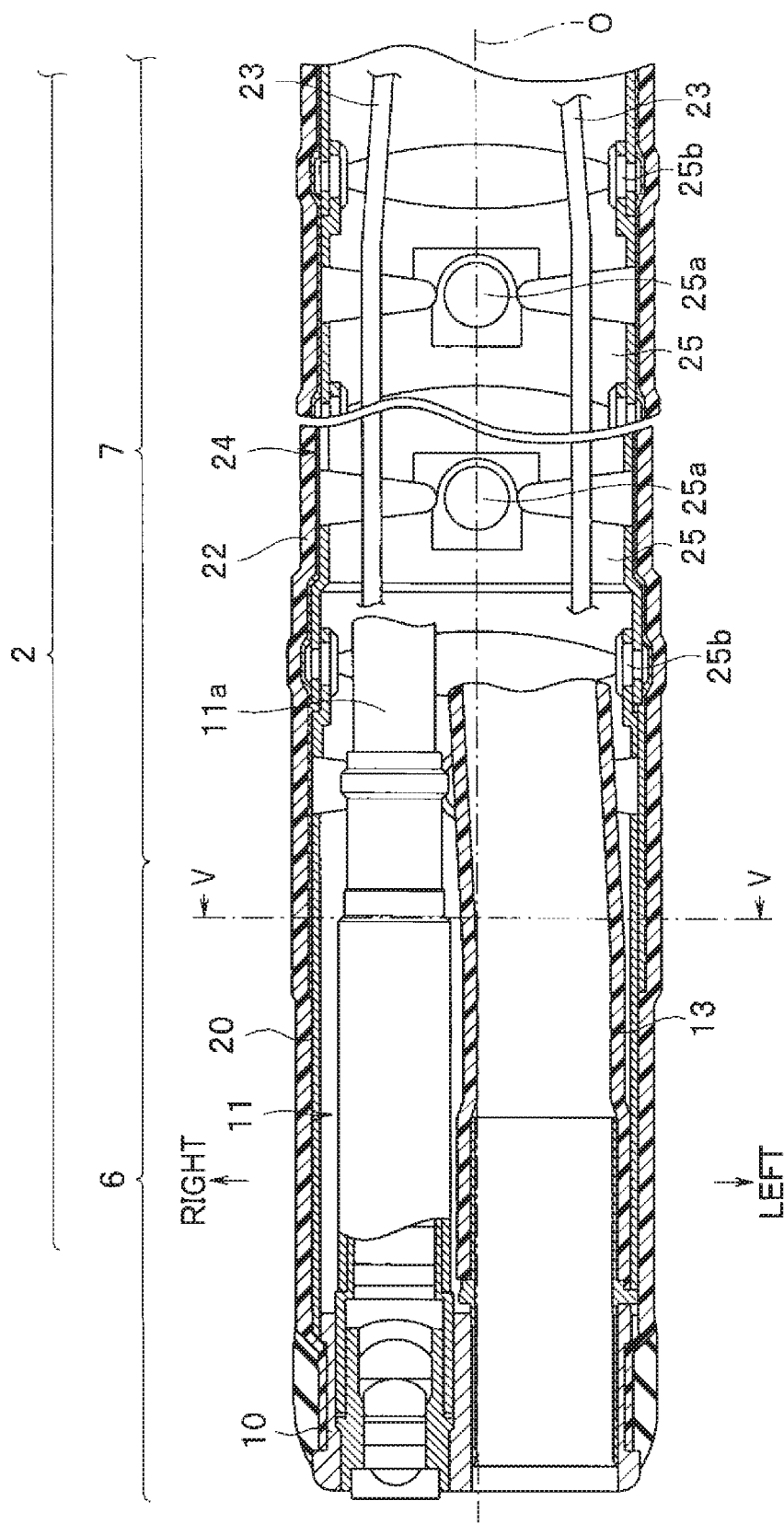
FIG. 4 is a fragmentary transverse cross-sectional view illustrating a tip portion and a bendable part of the endoscope depicted in FIG. 1.

As illustrated in FIG. 4, a metal-made, hard tip portion 10 is disposed in the tip portion 6. In this hard tip portion 10, (i) an imaging unit 11 with an imaging device such as CCD or CMOS accommodated therein, (ii) a pair of light guides (not illustrated) and (iii) the surgical instrument insertion channel 13 are held. In the tip portion 6, a most distal bending element 20 of a substantially cylindrical shape is externally fitted on the side of a proximal end of the hard tip portion 10. The most distal bending element 20 is covered at an outer circumference thereof with a bending rubber 22. On an inner circumference of the most distal bending element 20, wire anchors (not illustrated) are disposed at four locations about the insertion axis "O". On the respective wire anchors, pulling wires are inserted in the insertion section 2. Four wires 23 a, 23 b, 23 c, and 23d are attached at distal ends thereof as pulling wires. The pulling wires 23 a, 23 b, 23 c, and 23d are connected at the distal ends thereof to the most distal bending element 20 of the bendable part 7. The pulling wires cause bending of the bendable part 7 when pulled or relaxed. It is to be noted that in FIG. 4, the pulling wires are designated by simply using numeral 23. The bendable part 7 is configured to be actively bendable in all directions around the insertion axis "O", including up-down/right-left directions, according to operational inputs to the operation unit 3 by a user or the like. Described specifically, the bendable part 7 in this embodiment is configured including a set 24 of bending elements. Multiple bending elements 25 are connected by alternately interposing pivots 25 a and pivots 25 b. The pivots 25 a are disposed in the up-down direction of the insertion section 2. The Pivots 25 b are disposed in the left-right direction of the insertion section 2.

A signal cable 11a, the light guide, and the surgical instrument insertion channel 13 all of which are inserted inside the set 24 of bending elements. The signal cable 11a, the light guide, and the surgical instrument insertion channel 13 are arranged in substantially the same arrangement as in the tip portion 6. The signal cable 11a extends from the imaging unit 11. The light guide is not illustrated. The predetermined one or more of the bending elements 25 make up the set 24 of bending elements. The respective bending operation wires or pulling wires are inserted through the wire guides (not illustrated). On each of the predetermined one or more of the bending elements 25, the wire guides are formed at positions where the arrangement of the wire guides in the direction of rotation about the insertion axis "O" is substantially the same as the above-described individual wire anchors (not illustrated). In addition, the set 24 of bending elements is covered at an outer circumference thereof with the bending rubber 22. The bending rubber 22 extends from the side of the tip portion 6. The flexible tube part 8 is configured of a tubular member having passively bendable flexibility. Inside this flexible tube part 8, signal cable 11a, light guide (not illustrated) and the surgical instrument insertion channel 13 are inserted (all not illustrated in FIGS. 1 and 2). Next, the configurations of individual components accommodated in the operation unit 3 will be described in detail hereinafter.

Figure 5:
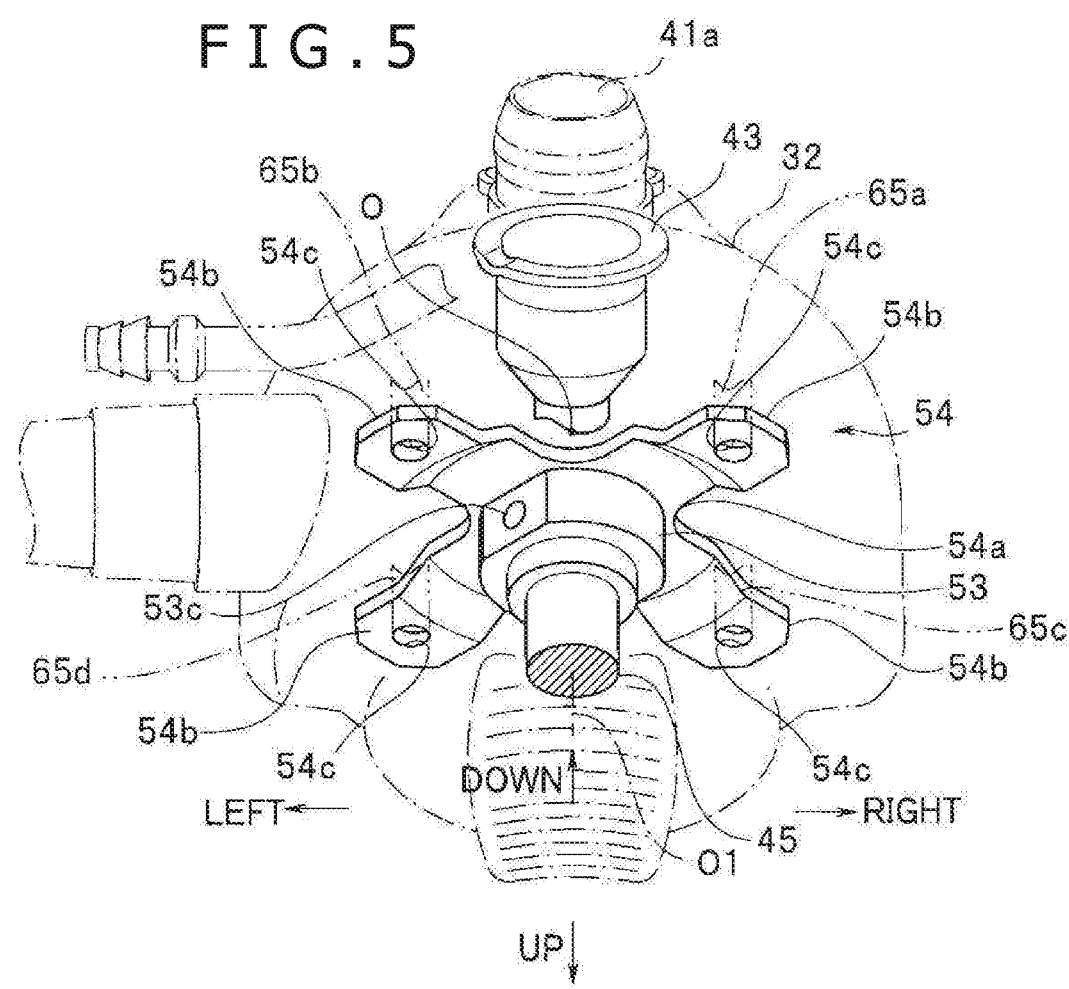
FIG. 5 is an illustration depicting an arrangement relationship between a wire pulling member and a cylinder in a bending operation device in the endoscope of FIG. 1.
Figure 9:
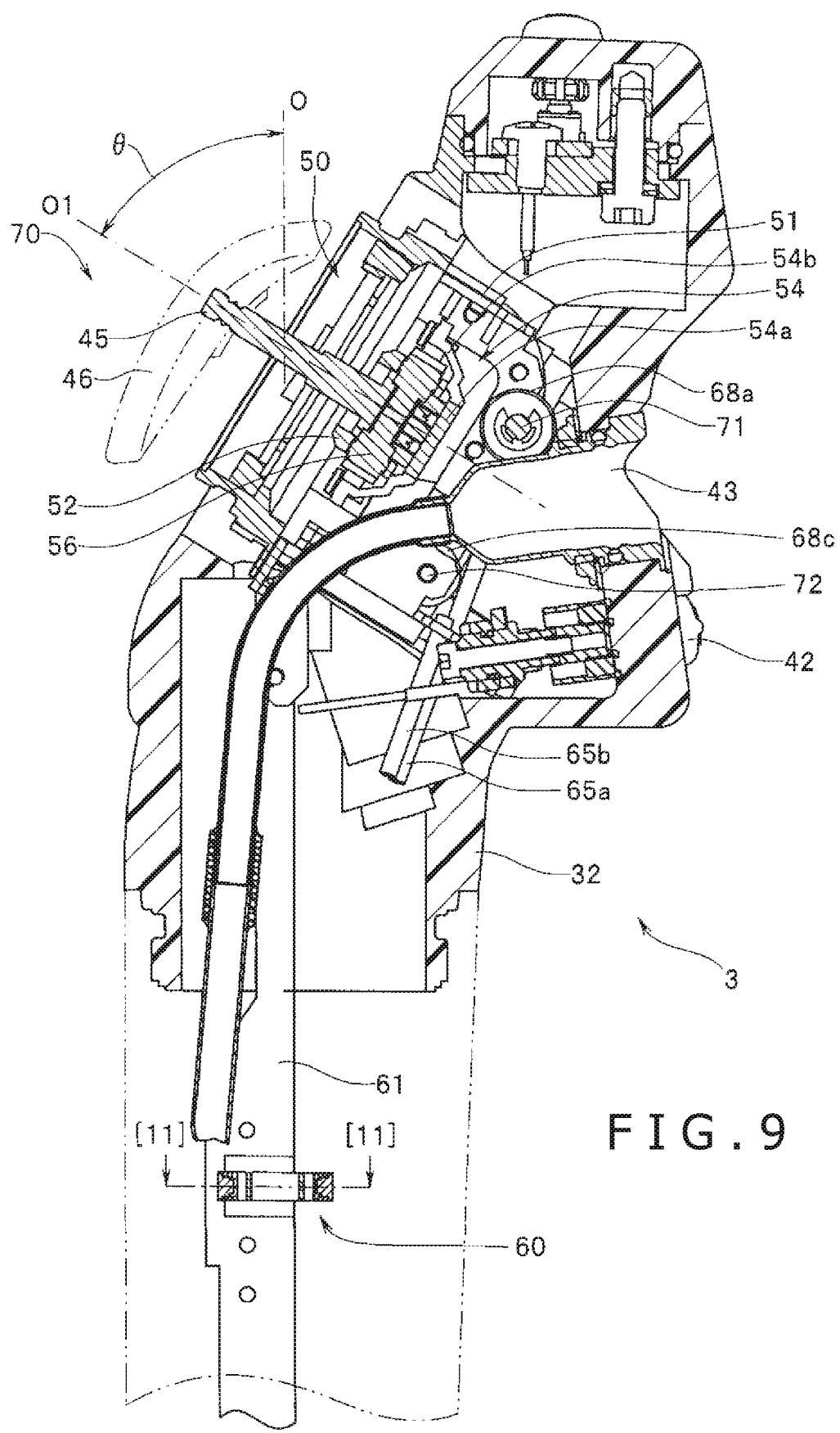
FIG. 9 is a fragmentary cross-sectional view of an operation unit of the endoscope of FIG. 1.

As illustrated in FIG. 5, a cylinder 43 is disposed inside the operation unit main body 32. The suction valve 41 can be consecutively disposed with the cylinder 43. This cylinder 43 allows detachable fitting of the suction valve 41. The cylinder 43 is arranged centrally in the horizontal width direction of the operation unit main body 32 so that on the insertion axis "O", the cylinder 43 lies corresponding to the arrangement of the suction button 41a. The bending lever 45 is configured of a joystick-type rod member that is tiltable in all directions including, for example, the up-down and left-right directions. This bending lever 45 is arranged on the side of the rear wall of the operation unit main body 32 at a position where the bending lever 45 is horizontally symmetrical. Described specifically, the bending lever 45 is arranged centrally in the horizontal wide direction of the operation unit main body 32 so that the bending lever 45 lies on the insertion axis "O". As illustrated in FIG. 9, the bending lever 45 is arranged with a lever axis O1 thereof extending at a preset angle θ with respect to the longitudinal direction of the operation unit main body 32 (the insertion axis "O") in a natural state (unloaded state; non-operated state).

Figure 6:
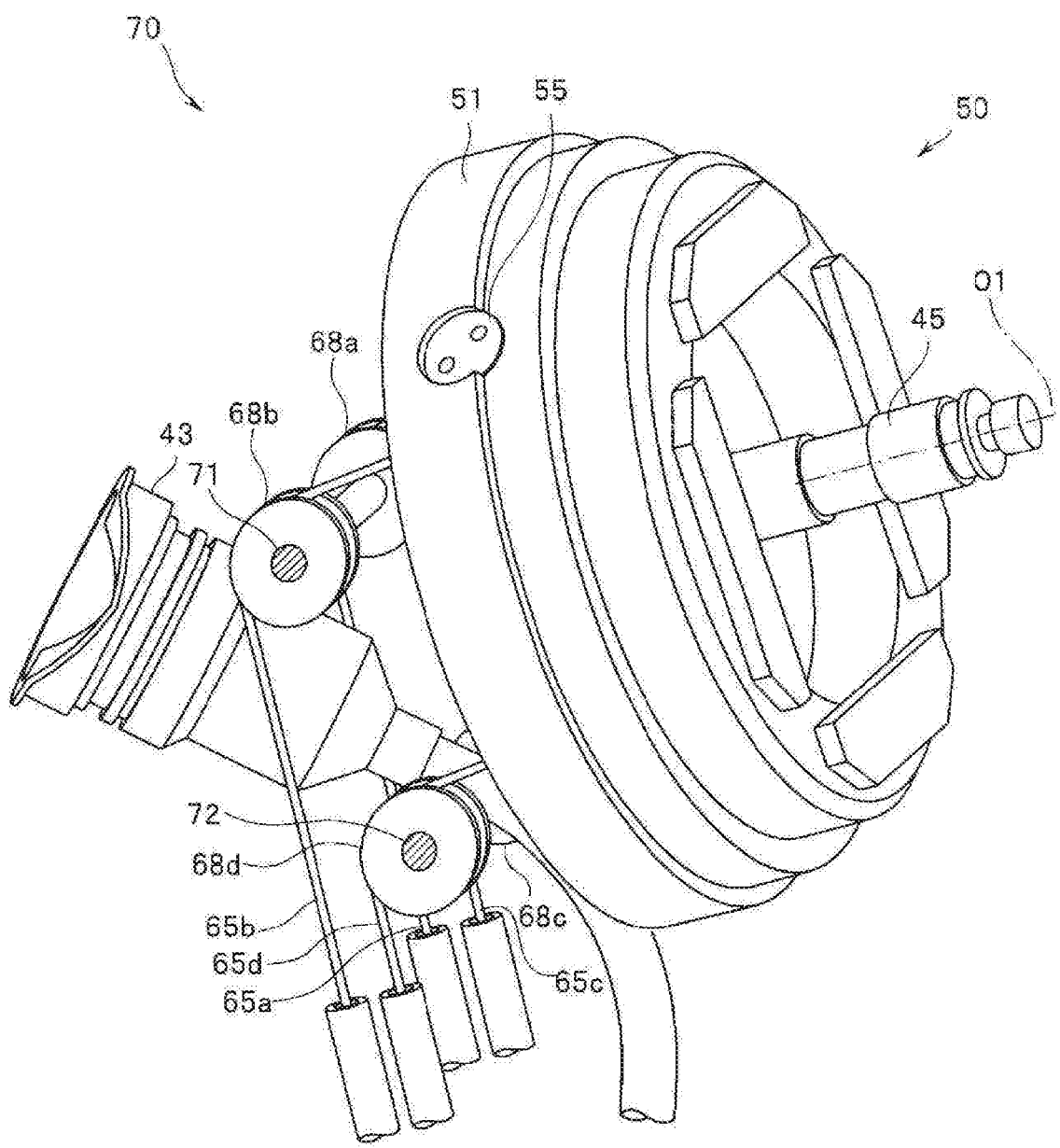
FIG. 6 is a perspective view illustrating an arrangement relationship between a wire pulling mechanism and the cylinder in the bending operation device in the endoscope of FIG. 1.
Figure 7:
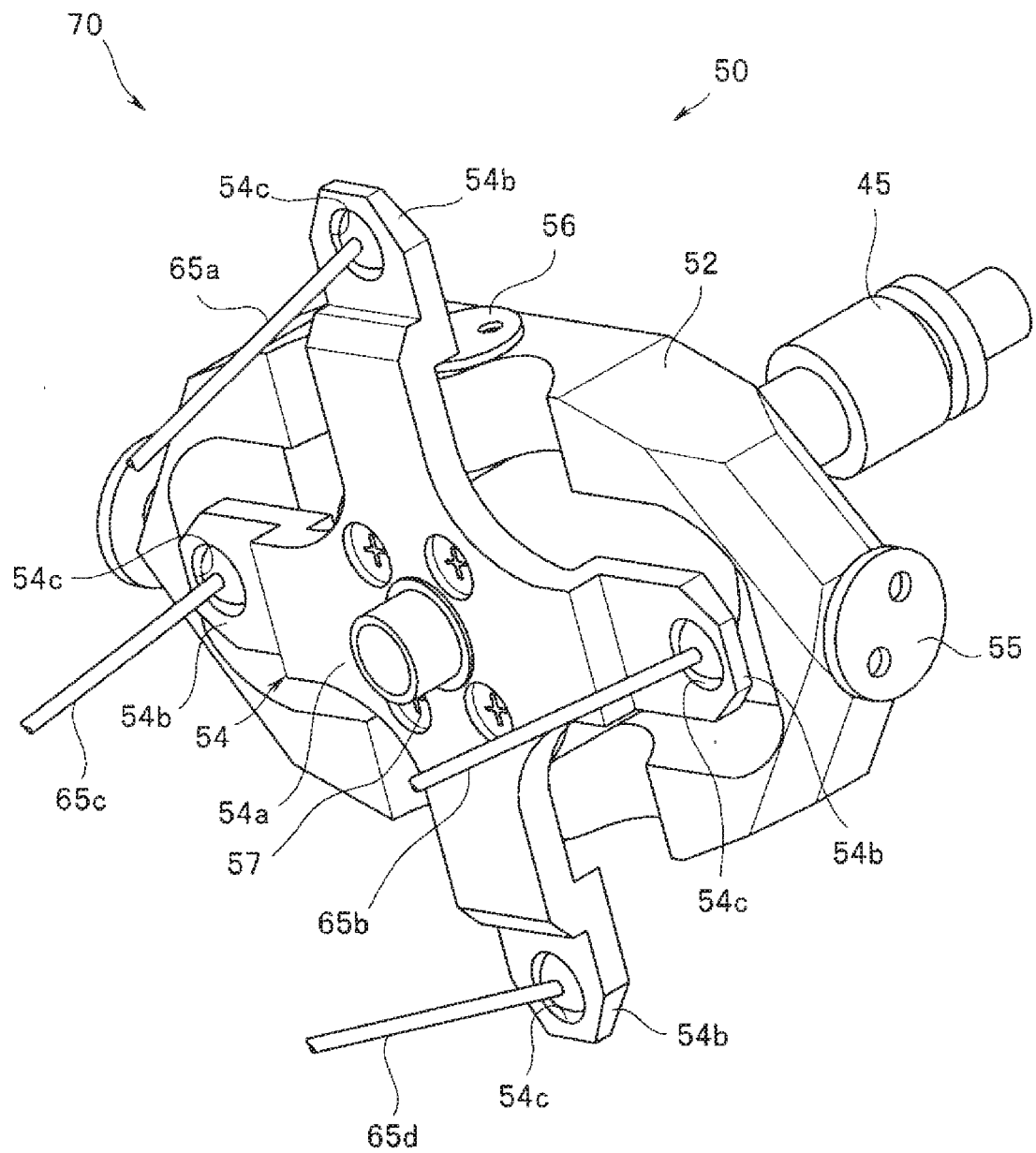
FIG. 7 is a perspective view illustrating an internal structure of the wire pulling mechanism in the bending operation device in the endoscope of FIG. 1.
Figure 8:
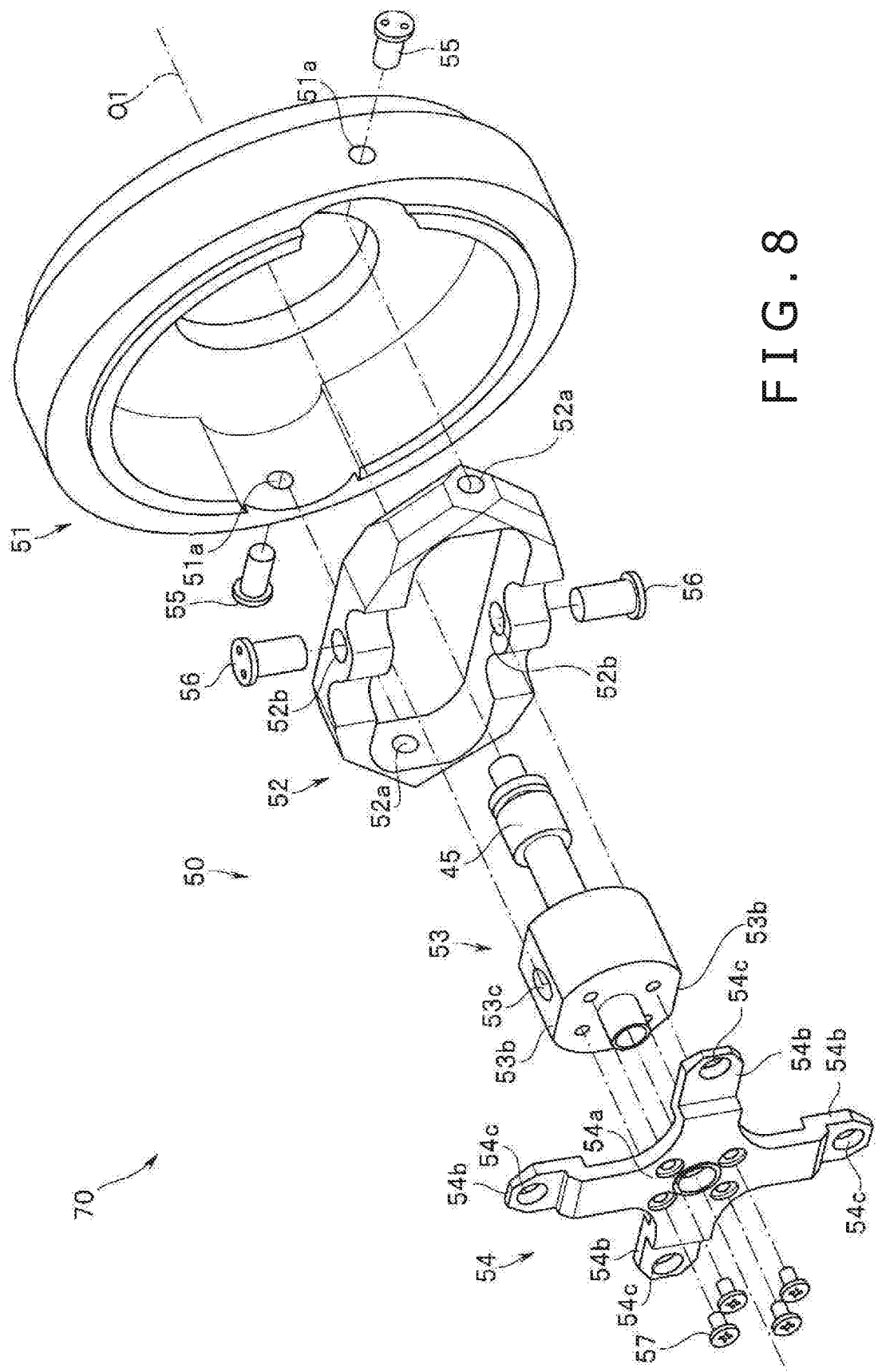
FIG. 8 is an exploded perspective view illustrating the internal structure of the wire pulling mechanism in the bending operation device in the endoscope of FIG. 1.

As illustrated in FIGS. 5 to 8, a wire pulling mechanism 50 is consecutively disposed on the side of a proximal end of the bending lever 45 within the operation unit 3. As will be described subsequently herein, the individual pulling wires 23 a, 23 b, 23 c, and 23 d on the side of the distal end of the insertion section 2 are connected to the wire pulling mechanism 50 via a relay disk mechanism 60 (not illustrated in FIGS. 5 to 8, see FIG. 9, etc.) as a connection member. Together with these wire pulling mechanism 50 and relay disk mechanism 60, the bending lever 45 makes up a bending operation device 70 (see FIG. 9) for allowing the bendable part 7 to undergo bending motion in a desired direction. The wire pulling mechanism 50 illustrated in FIGS. 6 to 8 includes a housing 51, a turnable frame 52, a base member 53, and a wire pulling member 54. The housing 51 is not illustrated in FIG. 7. The turnable frame 52 is not visible in FIG. 6. The turnable frame 52 is turnably or rockably supported in the housing 51. The base member 53 is turnably or rockably supported in the turnable frame 52 in FIG. 8. The wire pulling member 54 is not visible in FIG. 6. The wire pulling member 54 is attachedably disposed on the base member 53. The housing 51 is configured of a member having a substantially cylindrical shape. Through a circumferential wall of this housing 51, shank bores 51 a are formed opposite to one another, as illustrated in FIG. 8.

The turnable frame 52 is configured, for example, of a frame having a substantially rectangular shape. As illustrated in FIG. 8, through this turnable frame 52, mutually-opposing screw bores 52a are centrally formed in pair at opposite end portions in the direction of the longer sides. In addition, mutually-opposing screw shank bores 52b are centrally formed in pair at opposite end portions in the direction of the shorter sides. Screws 55 is inserted in the respective shank bores 51a of the housing 51. The screws 55 are maintained in threaded engagement with the respective screw bores 52a, whereby the turnable frame 52 is supported on the housing 51 turnably about an axis. The axis connects the respective screws 55, respective shank bores 51a and respective screw bores 52a. The base member 53 is configured of a member having a substantially cylindrical shape. On a central axis of the base member 53, the bending lever 45 is integrally formed. On the circumference of the base member 53, mutually-opposing flat portions 53b are formed in pair. Further, screw bores 53c are formed extending through the flat parts 53b in FIG. 8. Screws 56 are inserted in the respective shank bores 52b of the turnable frame 52. The screws 56 are maintained in threaded engagement with the screw bores 53c, whereby the base member 53 is supported on the turnable frame 52 turnably about an axis. The axis connects the screws 56, shank bores 52b and screw bores 53c. The base member 53 is supported on the housing 51 via the turnable frame 52 as described hereinbefore. The bending lever 45 is disposed integrally and consecutively with the base member 53. Therefore, the bending lever 45 can be tilted in a desired direction.

As illustrated in FIGS. 7 and 8, the wire pulling member 54 is configured of a plate-shaped member with arm portions 54b extending in four different directions from one another. More specifically, in this embodiment, the wire pulling member 54 is configured of a cruciform, plate-shaped member with the mutually-adjacent arm portions 54b set at angular intervals of 90 degrees. The wire pulling member 54 is attached at a central part 54a thereof on the base member 53 via multiple screws 57 (four screws in this embodiment). In other words, the bending lever 45 is connected to the wire pulling member 54 via the base member 53. As a consequence, the individual arm portions 54b are displaceable on the sides of distal ends thereof in response to tilting operation of the bending lever 45. On the sides of the distal ends of the individual arm portions 54b supported displaceable as described hereinbefore, wire fixing holes 54c are formed. In the respective wire fixing holes 54c, four operation wires 65a, 65b, 65c, and 65d are attached at one ends thereof. In other words, the operation wires 65a, 65b, 65c, and 65d are wire members, which are attached at one ends thereof to the arm portions 54b of the wire pulling member 54. The wire pulling member 54 is connected to the bending lever 45 or the bending operation member. The operation wires 65a, 65b, 65c, and 65d are pulled or relaxed according to displacement of the bending lever 45 or the bending operation member. Now, the individual operation wires 65a, 65b, 65c, and 65d are assumed to be arranged relative to the individual wire fixing holes 54c, for example, as illustrated in FIG. 5. Described specifically, the operation wires 65a and 65c are attached on the upper right arm portion 54b and lower right arm portion 54b illustrated in FIG. 5, respectively, so that the operation wires 65a and 65c are pulled when the bending lever 45 is tilted in a leftward tilting direction.

Similarly, the operation wires 65b and 65d are attached on the upper left arm portion 54b and lower left arm portion 54b illustrated in FIG. 5, respectively, so that the operation wires 65b and 65d are pulled when the bending lever 45 is tilted in a rightward tilting direction. Similarly, the operation wires 65a and 65b are attached on the upper right arm portion 54b and upper left arm portion 54b illustrated in FIG. 5, respectively, so that the operation wires 65a and 65b are pulled when the bending lever 45 is tilted in an upward tilting direction. Similarly, the operation wires 65c and 65d are attached on the lower right arm portion 54b and lower left arm portion 54b illustrated in FIG. 5, respectively, so that the operation wires 65c and 65d are pulled when the bending lever 45 is tilted in a downward tilting direction. The angles between the adjacent arm portions 54b are not limited to 90 degrees, but can be varied as desired, for example, within a range of ±30 degrees from the 90 degrees as a basis.

The wire pulling mechanism 50 is arranged so that it opposes the cylinder 43 in a front-to-rear relationship in the operation unit main body 32 in FIGS. 5 and 6). In this arrangement, the wire pulling mechanism 50 is arranged at a position where the arm portions 54b is each angularly shifted within a range of 30 degrees to 60 degrees about the lever axis O1 of the bending lever 45 relative to the corresponding up-down or left-right tilting direction set for the bending lever 45. The range can be set as 45 degrees. As a consequence, as illustrated in FIG. 5, for example, the wire pulling mechanism 50 is arranged in a state that the cylinder 43 can be seen between adjacent two of the arm portions 54b of the wire pulling member 54.

Figure 10:
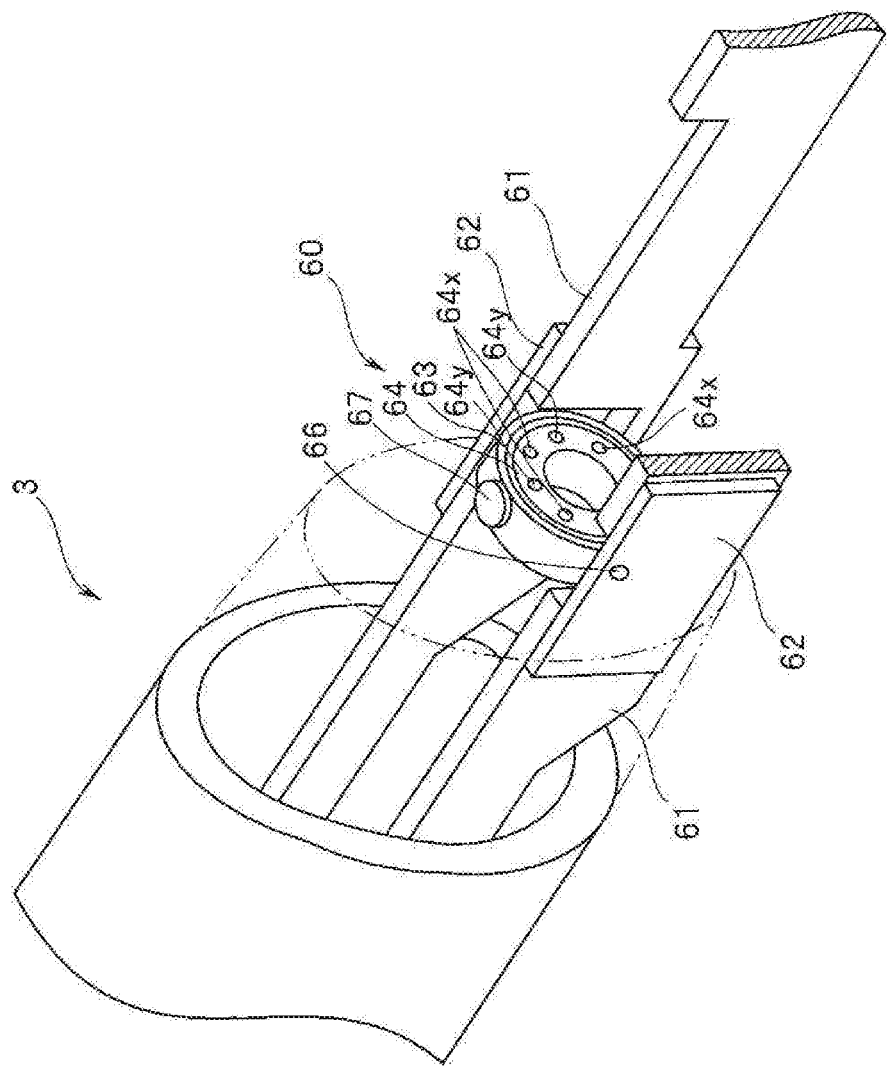
FIG. 10 is a view illustrating the arrangement of a relay disk mechanism in the operation unit of the endoscope of FIG. 1.
Figure 11:
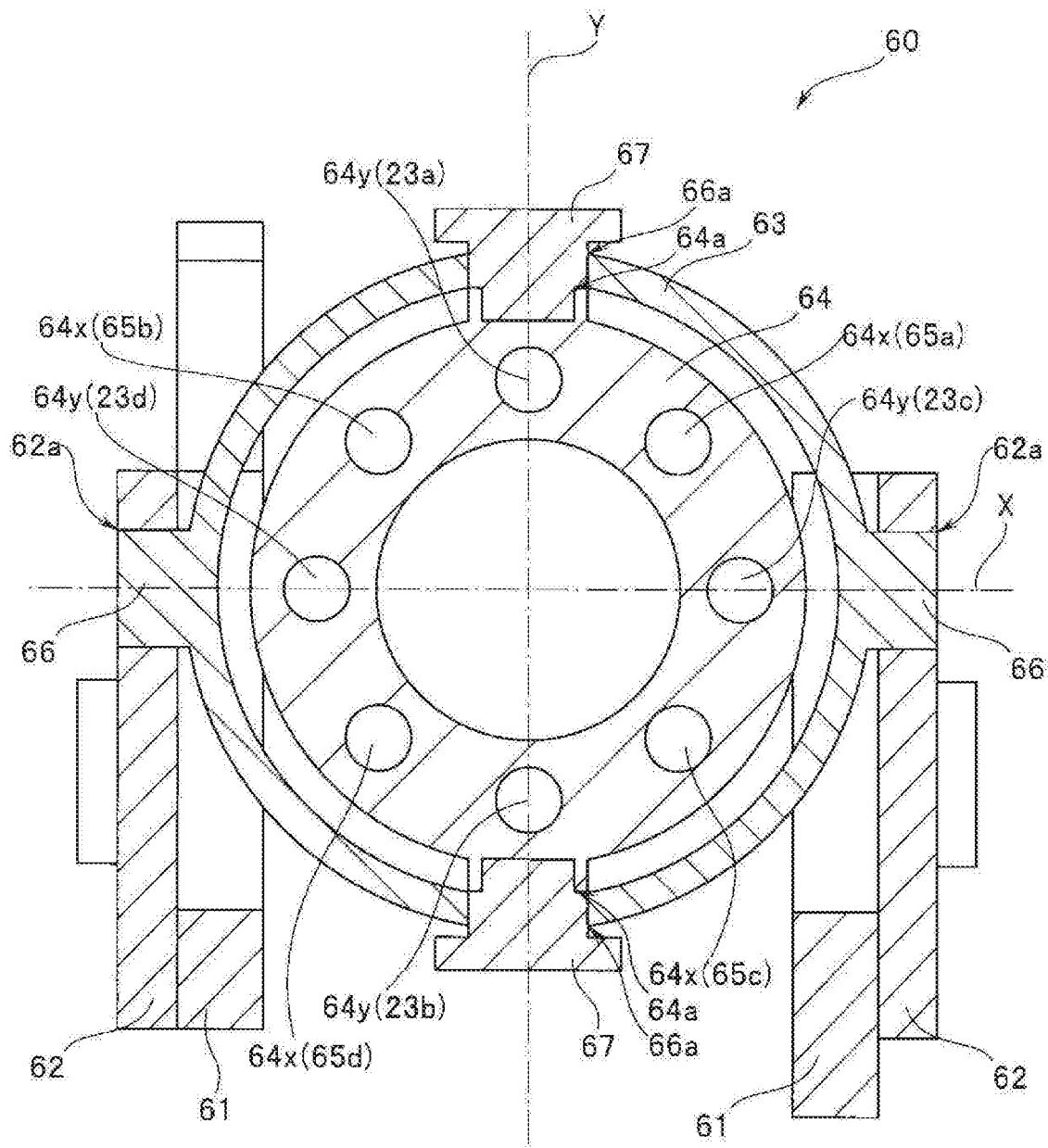
FIG. 11 is an enlarged fragmentary cross-sectional view illustrating a cross-section of the relay disk mechanism in the operation unit of the endoscope of FIG. 1 wherein the cross-sectional view is taken along line 11-11 of FIG. 9.

As illustrated in FIGS. 9, 10 and 11, the relay disk mechanism 60 is configured of combinations of stays 61 and 62, a housing 63, and a turnable frame 64. The stays extend in left and right pair from the inside of the operation unit main body 32 into the grip handle 33. The housing 63 is supported turnably or rockably on the stays 62. The turnable frame 64 is turnably or rockably supported in the housing 63. The relay disk mechanism 60 has substantially the same basic configuration as the above-described wire pulling mechanism 50. Described specifically, the relay disk mechanism 60 has a configuration that the housing 63 and turnable frame 64 are supported turnably or rockably about two axes. The two axes are orthogonal to the insertion axis "O" and also orthogonal to each other. The shafts 66 and screws 67 are inserted along the two axes. The two axes are set specifically X-axis and Y-axis in FIG. 11, as a support axis or turning center. The housing 63 is a first ring-shaped member configured of a member having a substantially ring shape. As illustrated in FIG. 11, on a circumferential wall of the housing 63, the shafts 66 are disposed in pair in a protruding manner. The shafts 66 are disposed at mutually-opposing positions and are formed to protrude outward in a radial direction or in the left-right direction. Through the circumferential wall of the housing 63, shank bores 66a are also formed at positions turned by an angle of approximately 90 degrees with respect to the paired shafts 66 so that they are arranged opposite to each other or in the up-down direction. The turnable frame 64 is a second ring-shaped member configured of a member having a substantially ring shape. In a peripheral wall of this turnable frame 64, as illustrated in FIG. 11, a pair of screw bores 64a are formed in a mutually-opposing manner at positions, which oppose the shank bores 66a when the relay disk mechanism 60 is brought into an assembled state.

The shafts 66 of the housing 63 are fitted in shaft bores 62a formed through the stays 62. As a consequence, the housing 63 is configured to be turnable or rockable about the X-axis depicted in FIG. 11 in a state that it is flanked by the pair of stays 62. Here, the X-axis is an axis that connects the respective shafts 66 and shaft bores 62a together. In the shank bores 66a of the housing 63, the screws 67 are inserted. The screws 67 are in threaded engagement with the screw bores 64a of the turnable frame 64. As a consequence, the turnable frame 64 is configured to be turnable or rockable relative to the housing 63 about the Y-axis depicted in FIG. 11. Here, the Y-axis is an axis that connects the respective screws 67, shank bores 66a and screw bores 64a together. The Y-axis and X-axis are axes orthogonal to each other in a plane in which the housing 63 and turnable frame 64 lie. Here, it is to be noted that the expression "the plane in which the housing 63 and turnable frame 64 lie" means a plane in which both of the members 63 and 64 have a substantially circular cross-section in FIG. 11. Based on the configuration described hereinbefore, the housing 63 or the first ring-shaped member is disposed rockably together with the turnable frame 64 or the second ring-shaped member in the same direction with the pair of shafts 66 serving as a support axis or the X-axis. The shafts 66 are disposed in a protruding manner on an outer circumference and are arranged opposite to each other. On the other hand, the turnable frame 64 or the second ring-shaped member is disposed rockably independently of the housing 63 or the first ring-shaped member with the Y-axis serving as a support axis. The Y-axis is orthogonal to the pair of shafts 66 of the housing 63, the support axis for the first ring-shaped member or the X-axis.

In the above-described embodiment, the housing 63 is configured to include the shafts 66 and to be turnable or rockable about the X-axis relative to the pair of stays 62 with the shafts 66 serving as a support axis, but the housing 63 should not be limited to this example. For example, the housing 63 may be configured to include a pair of holes in an outer circumference thereof at positions opposite to each other and to be turnable or rockable about the X-axis relative to the pair of stays 62 via screws inserted through the paired holes. Further, the pair of shafts 66 is exemplified in the form that they are disposed in a protruding manner on the outer circumference, but should not be limited to the exemplified form and may be contemplated to have a form that they are disposed in an inwardly protruding manner. The turnable frame 64 includes multiple holes 64*x* and 64*y* formed at preset intervals in a circumferential direction. This embodiment exemplifies the arrangement of four holes 64*x* and four holes 64*y* as the plural holes 64*x* and 64*y*. Described specifically, the four operation wires 65*a*, 65*b*, 65*c*, and 65*d* extend from the side of the operation unit. The four operation wires are attached at the other ends thereof in the four holes 64*x* out of the plural holes 64*x* and 64*y*. The four operation wires 65*a*, 65*b*, 65*c*, and 65*d* that extend from the side of the operation unit are the wires, which are attached at the one ends thereof in the wire fixing holes 54*c* of the respective arm portions 54*b* of the wire pulling member 54 and extend to the relay disk mechanism 60. To the wire fixing holes 54*c* of the respective arm portions 54*b* of the wire pulling member 54, the operation wires 65*a*, 65*b*, 65*c*, and 65*d* are connected on the side of the proximal ends thereof. To the four holes 64*x* of the turnable frame 64, on the other hand, the operation wires 65*a*, 65*b*, 65*c*, and 65*d* are connected on the side of the distal ends thereof.

Described in more detail, in the four holes 64*x* of the turnable frame 64, the individual ones of the operation wires 65*a*, 65*b*, 65*c*, and 65*d* are attached corresponding to the wire fixing holes 54*c* of the respective arm portions 54*b* of the wire pulling member 54. To have the operation wires 65*a* and 65*c* pulled when the bending lever 45 is tilted in the leftward tilting direction, for example, the operation wires 65*a* and 65*c* are attached in the upper right hole 64*x* and lower right hole 64*x* depicted in FIG. 11, respectively. Similarly, to have the operation wires 65*b* and 65*d* pulled when the bending lever 45 is tilted in the rightward tilting direction, the operation wires 65*b* and 65*d* are attached in the upper left hole 64*x* and lower left hole 64*x* depicted in FIG. 11, respectively. Similarly, to have the operation wires 65*a* and 65*b* pulled when the bending lever 45 is tilted in the upward tilting direction, the operation wires 65*a* and 65*b* are fixed in the upper right hole 64*x* and upper left hole 64*x* depicted in FIG. 11, respectively. Similarly, to have the operation wires 65*c* and 65*d* pulled when the bending lever 45 is tilted in the downward tilting direction, the operation wires 65*c* and 65*d* are attached in the lower right hole 64*x* and lower left hole 64*x* depicted in FIG. 11, respectively. Further, the four wires 23*a*, 23*b*, 23*c*, and 23*d* extend toward the distal end of the insertion section 2. The four wires 23*a*, 23*b*, 23*c*, and 23*d* are attached on the wire anchors (not illustrated) on the most distal bending element 20 in the bendable part 7. The four wires 23*a*, 23*b*, 23*c*, and 23*d* are attached at the other ends thereof in the four holes 64*y* out of the plural holes 64*x* and 64*y*. Four pulleys 68*a*, 68*b*, 68*c*, and 68*d* are rotatably supported on axles 71 and 72 in the operation unit main body 32. The four pulleys are arranged at midway parts of the respective operation wires 65*a*, 65*b*, 65*c*, and 65*d*.

The four pulleys are configuration members for changing the extending directions of the four operation wires 65 *a*, 65 *b*, 65 *c*, and 65 *d*, which are connected to the respective arm portions 54 *b* of the wire pulling member 54, inside the operation unit 3. To the four holes 64 *y* of the turnable frame 64, the pulling wires 23 *a*, 23 *b*, 23 *c*, and 23*d* are connected on the sides of the proximal ends thereof. The sides of the distal ends of respective pulling wires 23 *a*, 23 *b*, 23 *c*, and 23*d* are attached on the wire anchors (not illustrated) on the most distal bending element 20 in the bendable part 7 as described hereinbefore. To have the pulling wire 23 *c* pulled by pulling of the operation wires 65 *a* and 65 *c* when the bending lever 45 is tilted in the leftward tilting direction, for example, the pulling wire 23 *c* is attached in the right hole 64 *y* depicted in FIG. 11. Similarly, to have the pulling wire 23*d* pulled by pulling of the operation wires 65 *b* and 65 *d* when the bending lever 45 is tilted in the rightward tilting direction, the pulling wire 23*d* is attached in the left hole 64 *y* depicted in FIG. 11. Similarly, to have the pulling wire 23 *a* pulled by pulling of the operation wires 65 *a* and 65 *b* when the bending lever 45 is tilted in the upward tilting direction, the pulling wire 23 *a* is attached in the upper hole 64 *y* depicted in FIG. 11. Similarly, to have the pulling wire 23 *b* pulled by pulling of the operation wires 65 *c* and 65 *d* when the bending lever 45 is tilted in the downward tilting direction, the pulling wire 23 *b* is attached in the lower hole 64 *y* depicted in FIG. 11.

Described simply, at the turnable frame 64 of the relay disk mechanism 60 as a connection member, the operation wires 65 *a*, 65 *b*, 65 *c*, and 65 *d* are connected at the other ends thereof to the holes 64 *x* as first positions. The pulling wires 23 *a*, 23 *b*, 23 *c*, and 23*d* are connected at the proximal ends thereof to the holes 64 *y* as second positions. The second positions are located at positions shifted by a predetermined angle from the holes 64 *x* or the first positions in a turning direction about the insertion axis "O" or the longitudinal axis of the operating unit 3. The pulling wires 23 *a*, 23 *b*, 23 *c*, and 23*d* are held displaceable according to pulling or relaxing of the operation wires 65 *a*, 65 *b*, 65 *c*, and 65 *d*. If in the configuration described hereinbefore, the user holds the grip handle 31 of the operation unit 3 and tilts the bending lever 45 in the leftward tilting direction with the thumb of the holding hand, for example, primarily the two operation wires 65 *a* and 65 *c* are pulled because the two operation wires 65 *a* and 65 *c* are connected to the two arm portions 54 *b* that are located in the rightward tilting direction. The pulling of these two operation wires 65 *a* and 65 *c* is transmitted to the corresponding two holes 64 *x* of the turnable frame 64, whereby the turnable frame 64 rocks over an angle corresponding to the pull/relax amount of the operation wires 65 *a* and 65 *c*. At this time, the rocking motion of the turnable frame 64 results in pulling of the pulling wire 23 *c*. The pulling wire 23 *c* is located on the left side as viewed in the bending direction. Therefore, in the bendable part 7, the pulling wire 23 *c* is pulled by the turnable frame 64, and the bendable part 7 is bent to leftward. If the user holds the grip handle 31 of the operation unit 3 and tilts the bending lever 45 in the rightward tilting direction with the thumb of the holding hand, for example, primarily the two operation wires 65 *b* and 65 *d* are pulled because the two operation wires 65 *b* and 65 *d* are connected to the two arm portions 54 *b* located in the leftward tilting direction.

The pulling of these two operation wires 65 *b* and 65 *d* is transmitted to the corresponding two holes 64 *x* of the turnable frame 64, whereby the turnable frame 64 rocks over an angle corresponding to the pull/relax amount of the operation wires 65 *b* and 65 *d*. At this time, the rocking motion of the turnable frame 64 results in pulling of the pulling wire 23 *d*. The pulling wire 23*d* is located on the left side as viewed in the bending direction. Therefore, in the bendable part 7, the pulling wire 23*d* is pulled by the turnable frame 64, and the bendable part 7 is bent rightward. If the user holds the grip handle 31 of the operation unit 3 and tilts the bending lever 45 in the upward tilting direction with the thumb of the holding hand, for example, primarily the two operation wires 65 *c* and 65 *d* are pulled because the two operation wires 65 *c* and 65 *d* are connected to the two arm portions 54 *b* located in the downward tilting direction. The pulling of these two operation wires 65 *c* and 65 *d* is transmitted to the corresponding two holes 64 *x* of the turnable frame 64, whereby the turnable frame 64 rocks over an angle corresponding to the pull/relax amount of the operation wires 65 *c* and 65 *d*. At this time, the rocking motion of the turnable frame 64 results in pulling of the pulling wire 23 *b*. The pulling wire 23 *b* is located on the down side as viewed in the bending direction. Therefore, in the bendable part 7, the pulling wire 23 *b* is pulled by the turnable frame 64, and the bendable part 7 is bent downward. If the user holds the grip handle 31 of the operation unit 3 and tilts the bending lever 45 in the downward tilting direction with the thumb of the holding hand, for example, primarily the two operation wires 65 *a* and 65 *b* are pulled because the two operation wires 65 *a* and 65 *b* are connected to the two arm portions 54 *b* located in the upward tilting direction.

The pulling of these two operation wires 65 *a* and 65 *b* is transmitted to the corresponding two holes 64 *x* of the turnable frame 64, whereby the turnable frame 64 rocks over an angle corresponding to the pull/relax amount of the operation wires 65 *a* and 65 *b*. At this time, the rocking motion of the turnable frame 64 results in pulling of the pulling wire 23 *a*. The pulling wire 23 *a* is located on the up side as viewed in the bending direction. Therefore, in the bendable part 7, the pulling wire 23 *a* is pulled by the turnable frame 64, and the bendable part 7 is bent upward. According to the above-described embodiment, the endoscope includes the bending operation device that allows the bendable part to undergo bending motion in response to tilting operation of the bending operation member. The bending lever 45 is disposed in the operation unit 3 and is tiltably supported. The bendable part 7 is disposed on the side of the distal end of the operation unit 3. To make the bendable part 7 bendable by tilting the bending lever 45 or the bending operation member in a predetermined direction, the bending operation device is configured by disposing the relay disk mechanism 60 or the connection member at midway parts of the wire members. The wire members connect between the bending lever 45 as the bending operation member and the bendable part 7. In this embodiment, the operation wires 65 *a*, 65 *b*, 65 *c*, and 65 *d* are connected at the one ends thereof to the bending lever 45 or the bending operation member, and are connected at the other ends thereof to the holes 64 *x* as the first positions on the turnable frame 64 of the relay disk mechanism 60 or the connection member.

On the other hand, the pulling wires 23 *a*, 23 *b*, 23 *c*, and 23 *d* are connected at the distal ends thereof to the bendable part 7, and are connected at the proximal ends thereof to the holes 64 *y* as the second positions. The second positions are located at the positions shifted by the preset angle in the turning direction about the insertion axis "0" or the longitudinal axis from the above-described holes 64 *x* or the first positions of the turnable frame 64 of the relay disk mechanism 60 or the connection member. The turnable frame 64 of the relay disk mechanism 60 or the connection member can bend the bendable part 7 by undergoing displacement according to the pull/relax amount of the operation wires 65 *a*, 65 *b*, 65 *c*, and 65 *d*. The operation wires are pulled or relaxed according to displacement of the bending lever 45 or the bending operation member. As a consequence, the inclusion of the relay disk mechanism can facilitate to change (i) the arrangement of the operation wires on the side of the bending operation member and (ii) the arrangement of the pulling wires on the side of the bendable part so that they can be arranged in a different way. It is, therefore, possible (i) to provide wider freedom of a layout upon arranging configuration members of a suction mechanism and various other configuration members such as the light guide in the operation unit and also (ii) to realize an efficient layout in the operation unit, so that downsizing of the operation unit itself can be realized. In the bending operation device of the above-described embodiment, the example that the shape of the turnable frame 64 in the relay disk mechanism 60 is configured to be circular is illustrated. However, one of ordinary skill in the art would appreciate that the turnable frame 64 is not limited to this shape and other shapes or configurations are within the scope of the invention. For example, relay disk mechanisms can be configured with turnable frames of such shapes as will be described hereinafter.

Figure 12:
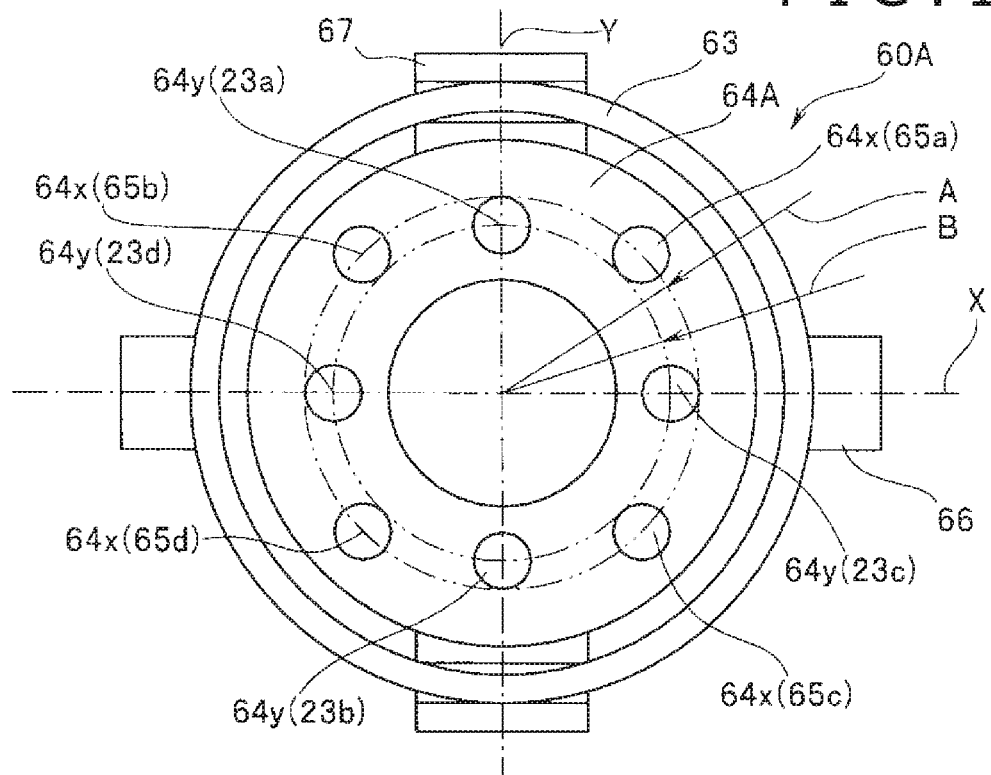
FIG. 12 is a view illustrating a first alternative modification of the relay disk mechanism in the bending operation device according to the present disclosure.

FIG. 12 is a view illustrating a first modification of the relay disk mechanism in the bending operation device according to the present disclosure. As illustrated in FIG. 12, a relay disk mechanism 60A of this modification basically has substantially the same configuration as the relay disk mechanism 60 in the bending operation device of the above-described embodiment. In the relay disk mechanism 60 in the above-described embodiment, the multiple holes 64*x* or the first positions and the multiple holes 64*y* or the second positions are arranged in or on the turnable frame 64 and are configured to be arranged on the same circle. In the relay disk mechanism 60A of this modification, on the other hand, multiple holes 64*x* or first positions and plural holes 64*y* or second positions are arranged in or on a turnable frame 64A and are configured to be arranged on concentric circles having different radii.

Specifically, as illustrated in FIG. 12, the multiple holes 64*x* as the first positions are formed on a circle indicated by a radius A in the turnable frame 64A. The operation wires 65*a*, 65*b*, 65*c*, and 65*d* are connected to the multiple holes 64*x* at the other ends thereof. Here, the multiple holes 64*x* are formed on the circle of the radius "A" in FIG. 12 at positions turned by an angle of approximately 30 degrees to 60 degrees relative to the respective positive, upward, downward, leftward and rightward directions as the tilting directions of the bending lever 45, in other words, the X-axis direction and Y-axis direction depicted in FIG. 12.

On the other hand, the multiple holes 64 *y* as the second positions are formed on another circle indicated by a radius "B" in the turnable frame 64A. The pulling wires 23 *a*, 23 *b*, 23 *c*, and 23*d* are connected to the multiple holes 64 *y* at the proximal ends thereof. Here, the radius "A" and radius "B" are assumed to satisfy the following inequality: radius "A">radius "B">0. In this modification, the multiple holes 64 *y* are formed on the circle of the radius "B" in FIG. 12 at positions where the circle intersects the respective positive, upward, downward, leftward and rightward directions as the tilting directions of the bending lever 45, in other words, the X-axis and Y-axis depicted in FIG. 12. Based on the configuration described hereinbefore, the pull amount of the wires on the side of the operation unit is increased by A/B times in the first modification. As a result, the arrangement of the pulling wires 23 *a*, 23 *b*, 23 *c*, and 23 *d* on the side of the insertion section can be confined compact while maintaining the pull amount as needed so that further downsizing of the operation unit 3 can be realized.

Figure 13:
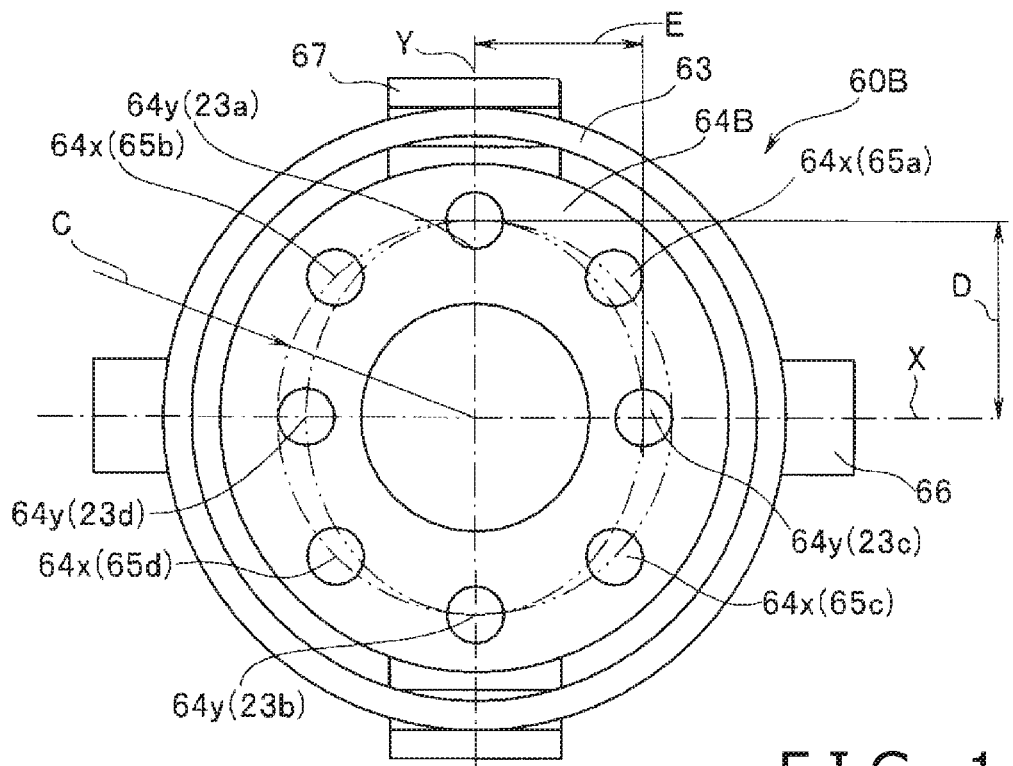
FIG. 13 is a view illustrating a second alternative modification of the relay disk mechanism in the bending operation device according to the present disclosure.

Further, FIG. 13 is a view illustrating a second modification of the relay disk mechanism in the bending operation device according to the present disclosure.

A relay disk mechanism 60B in the second modification as illustrated in FIG. 13 is configured so that the arrangements of plural holes 64*x* or first positions and plural holes

64y or second positions placed in or on a turnable frame 64B are set as will be described hereinafter.

Specifically, as illustrated in FIG. 13, the multiple holes 64x as the first positions are formed on a circle indicated by a radius "C" in the turnable frame 64B of the relay disk mechanism 60B in this modification. The operation wires 65a, 65b, 65c, and 65d are connected to the plural holes 64x at the other ends thereof. Here, the multiple holes 64x are formed on the circle of the radius "C" in FIG. 13 at positions turned by an angle of approximately 30 degrees to 60 degrees relative to the respective positive, upward, downward, leftward and rightward directions as the tilting directions of the bending lever 45, in other words, the X-axis direction and Y-axis direction depicted in FIG. 13.

On the other hand, the multiple holes 64 y as the second positions are formed on an ellipse having a major axis of 2D and a minor axis of 2E when D>E>0 in the turnable frame 64B. The pulling wires 23 a, 23 b, 23 c, and 23d are connected to the multiple holes 64 y at the proximal ends thereof. Here, the multiple holes 64 y are formed on the ellipse in FIG. 13 at positions where the ellipse intersects the respective positive, upward, downward, leftward and rightward directions as the tilting directions of the bending lever 45, in other words, the X-axis and Y-axis depicted in FIG. 13.

As described hereinbefore, the turnable frame 64B in the second modification is formed so that the change ratio of a pull amount differs between the up-down tilting direction and the left-right tilting direction because the pulling wires 23 a, 23 b, 23 c, and 23 d on the side of the insertion section are arranged on the ellipse. Described specifically, the pull amount of the wires on the side of the operation unit is increased by D/C times in the up-down tilting direction and by E/C times in the left-right tilting direction. As a consequence, the pull amount can be set as needed in each direction without changing the size of the operation unit 3.

The present invention should not be limited to the above-described embodiment and modifications, and various modifications and applications are obviously feasible within a scope not departing from the scope of the present disclosure. Further, inventions at various stages are included in the above-described embodiment and modifications, and a variety of inventions can be drawn by suitable combinations of the plural features disclosed herein. If despite the deletion of one or more features from all the features presented in the above-described embodiment and modifications, the problem to be resolved by the present invention can be still resolved and the advantageous effects of the present invention are still available, for example, the configuration without such one or more features can be drawn as an invention. Furthermore, the features of the above-described embodiment and modifications may be suitably combined together. The present invention, except for restrictions thereto by the accompanying claims, should by no means be restricted by the specific embodiment and modifications.

The details disclosed by the above-described basic application for priority shall be interpreted as having been incorporated by reference in the description, claims and drawings of this application.

The present invention can be applied not only to endoscope control devices in the medical field, but also to endoscope control devices in the industrial field.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A bending operation device comprising:
   a bending operation member disposed in an operation unit and supported tiltably in a preset direction;
   a bendable part disposed on a side of a distal end of the operation unit;
   an operation wire connected at an end thereof to the bending operation member and configured to be pulled or relaxed according to displacement of the bending operation member;

a pulling wire connected at a distal end thereof to the bendable part and configured to bend the bendable part when pulled or relaxed; and a connection member including a turnable frame that is pivotable in a first direction around a first axis and is pivotable in a second direction around a second axis different from the first axis, the connection member being connected to an opposite end of the operation wire at a first position and connected to a proximal end of the pulling wire at a second position, the second position being shifted from the first position by a preset angle in a turning direction about a longitudinal axis of the operation unit, whereby the connection member is held displaceable according to pulling or relaxing of the operation wire.

2. The bending operation device of claim 1, wherein:
the connection member further includes a first ring-shaped member, and the turnable frame is a second ring-shaped member turnably supported inside the first ring-shaped member,
the first ring-shaped member is disposed rockably together with the second ring-shaped member in the first direction about a pair of shafts or a pair of holes arranged opposite to each other as the first axis, and
the second ring-shaped member is disposed rockably in the second direction independently of the first ring-shaped member about a shaft as the second axis, the shaft being orthogonal to the first axis for the first ring-shaped member.

3. The bending operation device of claim 1, wherein the first position and second position on the connection member are arranged on concentric circles.

4. The bending operation device of claim 1, wherein the first position on the connection member is arranged on a circle having a first radius, and the second position on the connection member is arranged on another circle having a second radius different from the first radius.

5. The bending operation device of claim 1, wherein the first position on the connection member is arranged on a circle, and the second position on the connection member is arranged on an ellipse.

6. An endoscope comprising:
an operation unit;
an insertion section disposed consecutively on a side of a distal end of the operation unit and formed in a shape of a slender tube; and
a bending operation device included inside the operation unit, wherein the bending operation device includes:
 a bending operation member disposed in an operation unit and supported tiltably in a preset direction;
 a bendable part disposed on a side of a distal end of the operation unit;
 an operation wire connected at an end thereof to the bending operation member and configured to be pulled or relaxed according to displacement of the bending operation member;
 a pulling wire connected at a distal end thereof to the bendable part and configured to bend the bendable part when pulled or relaxed; and
 a connection member including a turnable frame that is pivotable in a first direction around a first axis and is pivotable in a second direction around a second axis different from the first axis, the connection member being connected to an opposite end of the operation wire at a first position and connected to a proximal end of the pulling wire at a second position, the second position being shifted from the first position by a preset angle in a turning direction about a longitudinal axis of the operation unit, whereby the connection member is held displaceable according to pulling or relaxing of the operation wire.

7. The endoscope of claim 6, wherein:
the connection member further includes a first ring-shaped member, and the turnable frame is a second ring-shaped member turnably supported inside the first ring-shaped member,
the first ring-shaped member is disposed rockably together with the second ring-shaped member in the first direction about a pair of shafts or a pair of holes arranged opposite to each other as the first axis, and
the second ring-shaped member is disposed rockably in the second direction independently of the first ring-shaped member about a shaft as the second axis, the shaft being orthogonal to the first axis for the first ring-shaped member.

8. The endoscope of claim 6, wherein the first position and second position on the connection member are arranged on concentric circles.

9. The endoscope of claim 6, wherein the first position on the connection member is arranged on a circle having a first radius, and the second position on the connection member is arranged on another circle having a second radius different from the first radius.

10. The endoscope of claim 6, wherein the first position on the connection member is arranged on a circle, and the second position on the connection member is arranged on an ellipse.

11. The bending operation device of claim 1, wherein:
the first axis is orthogonal to the second axis, and
the first axis and the second axis are orthogonal to the longitudinal axis of the operation unit.

12. The endoscope of claim 6, wherein:
the first axis is orthogonal to the second axis, and
the first axis and the second axis are orthogonal to the longitudinal axis of the operation unit.

13. The bending operation device of claim 1, wherein:
the turnable frame is a first turnable frame,
the connection member further includes a second turnable frame in which the first turnable frame is turnably supported,
the second turnable frame is disposed rockably together with the first turnable frame in the second direction about a pair of shafts or a pair of holes arranged opposite to each other as the second axis, and
the first turnable frame is disposed rockably independently of the second turnable frame about a shaft as the first axis, the shaft being orthogonal to the second axis for the second turnable frame.

14. The endoscope of claim 6, wherein:
the turnable frame is a first turnable frame,
the connection member further includes a second turnable frame in which the first turnable frame is turnably supported,
the second turnable frame is disposed rockably together with the first turnable frame in the second direction about a pair of shafts or a pair of holes arranged opposite to each other as the second axis, and
the first turnable frame is disposed rockably independently of the second turnable frame about a shaft as the first axis, the shaft being orthogonal to the second axis for the second turnable frame.

* * * * *